United States Patent
Bartholomaeus et al.

(10) Patent No.: US 6,291,462 B1
(45) Date of Patent: Sep. 18, 2001

(54) ORAL MEDICINAL PREPARATIONS WITH REPRODUCIBLE RELEASE OF THE ACTIVE INGREDIENT GATIFLOXACIN OR ITS PHARMACEUTICALLY SUITABLE SALTS OR HYDRATES

(75) Inventors: Johannes Bartholomaeus, Aachen; Juergen Betzing, Loerrach, both of (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 09/700,055

(22) PCT Filed: Apr. 29, 1999

(86) PCT No.: PCT/EP99/02893

§ 371 Date: Feb. 16, 2001

§ 102(e) Date: Feb. 16, 2001

(87) PCT Pub. No.: WO99/58129

PCT Pub. Date: Nov. 18, 1999

(30) Foreign Application Priority Data

May 9, 1998 (DE) ............................................. 198 20 801

(51) Int. Cl.$^7$ .................................................. A61K 31/495
(52) U.S. Cl. ........................................................ 514/253.08
(58) Field of Search ........................................... 514/253.08

(56) References Cited

FOREIGN PATENT DOCUMENTS 0 230 295    7/1987   (EP) .

OTHER PUBLICATIONS

Chulia et al. (editors), "Power Technology and Pharmaceutical Processes", © 1994 Elsevier Science B.V.

Nakashima et al., "Single– and Multiple–Dose Pharmacokinetics of AM–1155, a New 6–Flouro–8–Methoxy Quinolone, in Humans", Antimicrobial Agents and Chemotherapy, Dec. 1995, pp. 2635–2640.

Ritschel, "Die Tablette", Der Pharmazeutische Betrieb Band 7 (1966) pp. 107–109 and 122–124.

List, "Arzneiformenlehre", p. 103 (section 4.8.3.1.1) (1976).

"Europäisches Arzneibuch", Section 2.9 (Methoden der pharmazeutischen Technologie), pp. 134–139 (1997) (with English translation).

*Primary Examiner*—Raymond Henley, III
(74) *Attorney, Agent, or Firm*—Crowell & Moring LLP

(57) ABSTRACT

Solid medicinal forms having a multiphase structure for oral administration, containing gatifloxacin or pharmaceutically acceptable salts or hydrates thereof and auxiliary substances selected from the group of fillers, binders, lubricants, disintegration aids and mixtures thereof, in which the inner phase contains the active ingredient gatifloxacin or pharmaceutically acceptable salts or hydrates thereof and auxiliary substances from the group of binders, fillers, disintegration aids and mixtures thereof, and at least one outer phase necessarily contains at least one disintegration aid and further auxiliary substances from the group of at least one lubricant, optionally fillers and/or optionally binders, and a process for the preparation of such solid medicinal forms.

13 Claims, No Drawings

ORAL MEDICINAL PREPARATIONS WITH REPRODUCIBLE RELEASE OF THE ACTIVE INGREDIENT GATIFLOXACIN OR ITS PHARMACEUTICALLY SUITABLE SALTS OR HYDRATES

This a 371 of PCT EP99/02893 filed Apr. 29, 1999.

BACKGROUND OF THE INVENTION

The invention relates to oral medicinal forms with reproducible disintegration time and release of the active ingredient fatifloxacin (1-cyclopropyl-6-fluoro-1,4-dihydro-8-methoxy-7-(3-methylpiperazin-1-yl)-4-oxoquinoline-3-carboxylic acid) or pharmaceutically acceptable salts or hydrates thereof, and to a process for their preparation.

Formulations in the form of solid individual medicinal forms, e.g. tablets, are prepared by compression. Tablets represent the most common and most important solid medicinal form in medical care. Examples which may be listed here are sublingual tablets, swallowing tablets, buccal tablets, effervescent tablets, ophthalmic tablets, quick-release tablets or coated tablets. These are prepared by compression from finely crystalline, powdered or granular drugs, normally with the addition of auxiliary substances.

The physical and chemical properties of the individual active ingredients are decisive for the preparation of tablets. The density, water content, crystalline form, surface structure, particle size, solubility, flow properties, hygroscopic nature and quality level of the active ingredient in question may be mentioned here. In particular, the water content, particle size, crystalline form and solubility of the active ingredients in question have a greater effect on the process for the preparation of tablets of high pharmaceutical quality (D. Chulia, M. Deleuil; Powder Technology and Pharmaceutical Process, 1994).

Tablets are prepared by the compression of powders or granules. Granulation is understood as meaning the conversion of small particles of powder to larger agglomerates. Tablets prepared from granules often have a greater mechanical strength than tablets compressed from powder. This is brought about by the uneven and rough surface of the granules; these have larger contact areas, giving rise to an increase in the adhesive forces. In the case of wet granulation, the granules are prepared from the primary particles with the aid of a liquid. The liquid, which can be selected from the group consisting of water, alcohols and polar or non-polar hydrocarbon compounds, usually also contains so-called binders, e.g. polyvinylpyrrolidone, pregelatinized starch or hydroxypropyl cellulose.

If tablets consist of granules, a distinction is made with this type of formulation between an inner phase and at least one outer phase. The inner phase comprises mostly the active ingredient and other auxiliary substances. This part is granulated in a wet or dry process and referred to as the inner phase of the ultimate compressed tablet. In the wet granulation process a defined amount of liquid is added to the mixture of substances and the whole is granulated. The ingredients of the so-called outer phase are auxiliary substances from the group consisting of binders, disintegration aids, lubricants and/or fillers. The two phases are mixed and then compressed to a solid medicinal form.

The disintegration time of tablets and the associated release of active ingredient is an important indicator of bioavailability in the human body.

The disintegration of tablets is a test method for providing evidence about a well-defined medicinal form. To determine the disintegration, tablets are placed in an apparatus, the main part of which generally consists of a rigid frame with a perforated bottom containing e.g. 6 cylindrical glass test tubes of fixed dimensions. Each tube can be fitted with a disc of a translucent plastic material or comparable materials which have specific orifices and V-shaped indentations. The test tubes are held vertical by an upper and a lower plate which can be made of plastic. On the underside there is a stainless steel wire gauze with a mesh size of 2 mm. The apparatus is moved uniformly up and down 28 to 32 times a minute by means of a motor. The apparatus is suspended in a vessel containing a suitable liquid. The amount of liquid present in the vessel should be such that the wire gauze is still immersed below the liquid surface at the highest point of its travel and is still above the bottom of the vessel at its lowest point, and the mouths of the tubes remain above the liquid surface. The liquid should be kept at a temperature of 36° C. to 38° C. The requirements are satisfied if disintegration occurs after a defined period of time (European Pharmacopoeia, Ph. Eur.). Examples of liquid media which can be used are water or artificial digestive juice at a given temperature (European Pharmacopoeia, Ph. Eur.).

Studies on the release of active ingredients are used to determine the dissolution rate of active ingredients from solid oral medicinal forms like tablets or capsules, as only the dissolved drug can be absorbed in the gastrointestinal tract. These studies are carried out under in vitro conditions, e.g. in water, artificial gastric juice with a pH of e.g. 1.2 or artificial intestinal juice with a pH of e.g. 6.8, at a temperature of 37° C., over a defined period of time (European Pharmacopoeia, Ph. Eur.). Vane stirrer or rotary basket apparatuses are used. Both of these consist of a vessel, a stirrer and a thermostatted bath. The vessel is covered with a flanged lid to prevent the test liquid from evaporating. There is a sampling orifice so that the concentration of the drug can be determined over time.

Formulations of solid medicinal forms with the active ingredient gatifloxacin or pharmaceutically acceptable salts or hydrates have already been described in EP-B 0 230 295. It was found that reproducible disintegration times and active ingredient release of the known tablet formulations are difficult to guarantee (cf. Table 1, Examples 1 to 4), the disintegration times of these solid formulations varying within a range of 3 minutes to 600 minutes.

SUMMARY OF THE INVENTION

The object of the present invention is to provide solid medicinal forms having reproducible disintegration times and active ingredient release and containing gatifloxacin or pharmaceutically acceptable salts or hydrates thereof as the active ingredient, together with auxiliary substances, and a process for their preparation.

It was found that the requirements for medicinal forms with reproducible disintegration time and active ingredient release, which contain gatifloxacin (1-cyclopropyl-6-fluoro-1,4-dihydro-8-methoxy-7-(3-methylpiperazin-1-yl)-4-oxoquinoline-3-carboxylic acid) or pharmaceutically acceptable salts or hydrates thereof as the active ingredient, are satisfied by the solid medicinal form according to the invention, which is prepared by means of granulation and has an inner phase and at least one outer phase.

The invention accordingly provides a solid medicinal form of multiphase structure for oral administration, which consists of an inner phase comprising the active ingredient is gatifloxacin (1-cyclopropyl-6-fluoro-1,4-dihydro-8-methoxy-7-(3-methylpiperazin-1-yl) -4-oxoquinoline-3- carboxylic-acid) or pharmaceutically acceptable salts or hydrates thereof and auxiliary substances from the group consisting of fillers, binders, disintegration aids and mixtures thereof, and at least one outer phase necessarily comprising at least one disintegration aid and further auxiliary substances from the group consisting of at least one lubricant, optionally fillers and/or optionally binders.

Solid medicinal forms which may be mentioned as examples are pellets, capsules, tablets or coated tablets. Tablets are used as the preferred solid medicinal form.

The granules obtained from the active ingredient gatifloxacin or pharmaceutically acceptable salts or hydrates, and auxiliary substances, form the inner phase. The pharmaceutical auxiliary substances used for the inner phase are taken from the group consisting of fillers, binders, disintegration aids and mixtures thereof.

There are no known solid formulations for the active ingredient gatifloxacin or pharmaceutically acceptable salts or hydrates which disintegrate completely over a period of 6 minutes to 30 minutes with a simultaneous active ingredient release of over 80% within this period.

DESCRIPTION OF PREFERRED EMBODIMENTS

The proportion of gatifloxacin or pharmaceutically acceptable salts or hydrates thereof is in the range between 20 wt. % and 80 wt. %, based on the total weight of the solid oral medicinal form. The preferred range is between 50 wt. % and 80 wt. %, based on the total weight of the solid oral medicinal form.

The term "fillers" is understood as meaning inter alia lactose, starch, dicalcium phosphate, microcrystalline cellulose, dextrose, mannitol or mixtures thereof.

Binders which can be used are hydroxypropyl methyl celluloses, polyvinylpyrrolidones, hydroxypropyl celluloses, starch mucilage or mixtures thereof.

Within the framework of the present invention, the group of disintegration aids includes hydroxypropyl celluloses with a low degree of substitution, crosspovidones, crosscarmellose, starches, pectins, alginates, surfactants or mixtures thereof. Celluloses from the group consisting of microcrystalline celluloses, hydroxypropyl celluloses, hydroxypropyl celluloses with a low degree of substitution, and mixtures thereof, are particularly preferred.

Pharmaceutical auxiliary substances from the group necessarily comprising at least one disintegration aid, at least one lubricant, optionally binders and/or optionally fillers are used as constituents of the outer phase.

Magnesium stearate, stearic acid, calcium stearate, fatty alcohols or mixtures thereof may be listed as examples of the group of lubricants used in the outer phase. It is preferable to use at least one disintegration aid and further auxiliary substances from the group consisting of at least one lubricant, optionally binders and/or optionally fillers in the outer phase.

The invention also provides a process for the preparation of solid multiphase medicinal forms for oral administration which contain gatifloxacin or pharmaceutically acceptable salts or hydrates thereof as the active ingredient and auxiliary substances from the group consisting of binders, lubricants, fillers and/or disintegration aids. The inner phase consists of gatifloxacin, pharmaceutically acceptable salts or hydrates thereof and auxiliary substances from the group consisting of binders, fillers and/or disintegration aids and mixtures thereof, which are converted to granules over 0.5 minute to 20 minutes in a mixing apparatus from the group consisting of mixers and kneaders, at a speed of rotation of 20 to 500 rpm (revolutions per minute), in the presence of a proportion of 20 wt. % to 80 wt. % of granulating liquid, based on the total amount of inner phase components used. The granules are then dried, sieved, mixed with auxiliary substances for at least one outer phase necessarily comprising at least one disintegration aid and further auxiliary substances from the group consisting of at least one lubricant, optionally binders and/or optionally fillers, which have not been cogranulated in the inner phase, and converted to a solid medicinal form. The tablet is the preferred solid medicinal form.

The preferred process is one in which a proportion of 20 wt. % to 70 wt. % of granulating liquid, based on the total amount of inner phase components used, and a mixer speed of 20 to 450 rpm, are used over 0.5 minute to 10 minutes for the inner phase of the solid medicinal form.

A particularly preferred process is one in which a proportion of 20 wt. % to 60 wt. % of granulating liquid, based on the total amount of inner phase components used, and a mixer speed of 20 to 400 rpm, are used over 1 minute to 7 minutes for the inner phase of the solid medicinal form.

A characteristic feature of the tablets prepared from granules by the process according to the invention is that they comprise at least 3 wt. % and at most 20 wt. % of one or more outer phases containing at least one lubricant, at least one disintegration aid, optionally binders and/or optionally fillers. A proportion in excess of 5 wt. % is preferred.

The mixing apparatuses used for the process belong to the group consisting of mixers and kneaders. Examples which may be mentioned are plough mixers or smaller mixers and kneaders from Lödige, Niro-Fielder or Baker-Perkins.

The disintegration times of Reference Examples 1 to 6 vary within a range of 3 minutes to 10 hours, as shown in Table 1. By contrast, the disintegration times of the medicinal form of Examples 7 to 14 according to the invention lie in a range of 6.5 minutes to 25 minutes, as shown in Table 2, making it possible to guarantee the reproducibility and therapeutic reliability.

TABLE 1

| Example | Hardness [N] | Disintegration time of the compressed product [min] |
|---------|--------------|-----------------------------------------------------|
| 1 | 140–150 | ~600.0 |
| 2 | 140–150 | 3.0 |
| 3 | 140–150 | 180.0 |
| 4 | 140–150 | 6.0 |
| 5 | 140–150 | 150.0 |
| 6 | 140–150 | 146.0 |

The release curves of Examples 1 to 4 have very different active ingredient release profiles. In the case of the release curves of Examples 1 and 3, only about 50% of the active ingredient is available within the first hour. Examples 2 and 4, on the other hand, show a complete active ingredient release despite the fact that the compressed product has the same formulation and the same constituents. The reproducibility of the active ingredient release from the known compositions is not guaranteed, with the possible consequence of a low level of release in the body over an undesirably long period of time.

TABLE 2

| Example | Hardness [N] | Disintegration time of the compressed product [min] |
|---|---|---|
| 7 | 140–150 | 6.5 |
| 8 | 140–150 | 8.8 |
| 9 | 140–150 | 7.5 |
| 10 | 140–150 | 16.5 |
| 11 | 140–150 | 9.5 |
| 12 | 140–150 | 18.5 |
| 13 | 140–150 | 20.5 |
| 14 | 140–150 | 25.0 |

The medicinal forms of Examples 7 to 14 according to the invention disintegrate completely over a period ranging from 6.5 minutes to 25 minutes. When looking at the release profile, an active ingredient release of at least 80% was observed within the first 30 minutes and a complete active ingredient release was observed after 60 minutes.

The solid medicinal form according to the invention guarantees the quality, in terms of pharmaceutical technology, of the hitherto unreproducible disintegration times and active ingredient release and the associated therapeutic reliability.

EXAMPLES

Granulation was performed in a Lödige FMS high-speed mixer and the tablets were prepared with a Fette eccentric press. The batch sizes were 800 g in each case.

The abbreviation "min" denotes minutes.

The abbreviation "rpm" denotes revolutions per minute.

Example 1

110.47 g of microcrystalline cellulose and 81 g of L-HPC (hydroxypropyl cellulose) were passed through a 0.8 mm sieve and the two substances were then mixed with 586.13 g of gatifloxacin (water content: 7.87 wt. %) in the high-speed mixer for 5 min. The mixture was granulated with 700 ml of an aqueous hydroxypropyl cellulose solution for 5 min at a mixer blade speed of 385 rpm. The moist granules were then passed through a 3 mm sieve and dried at 50° C. for approx. 17 hours. After the dried granules had been sieved again, 16.20 g of magnesium stearate were added and the mixture was compressed to tablets with a hardness of 140 to 150 N.

Example 2

110.47 g of microcrystalline cellulose and 81 g of L-HPC were passed through a 0.8 mm sieve and the two substances were then mixed with 586.13 g of gatifloxacin (water content: 7.87 wt. %) in the high-speed mixer for 5 min. The mixture was granulated with 500 ml of an aqueous hydroxypropyl cellulose solution for 1 min at a mixer blade speed of 215 rpm. The moist granules were then passed through a 3 mm sieve and dried at 50° C. for approx. 17 hours. After the dried granules had been sieved again, 16.20 g of magnesium stearate were added and the mixture was compressed to tablets with a hardness of 140 to 150 N.

Example 3

110.47 g of microcrystalline cellulose and 81 g of L-HPC were passed through a 0.8 mm sieve and the two substances were then mixed with 586.13 g of gatifloxacin (water content: 7.87 wt. %) in the high-speed mixer for 5 min. The mixture was granulated with 700 ml of an aqueous hydroxypropyl cellulose solution for 5 min at a mixer blade speed of 215 rpm. The moist granules were then passed through a 3 mm sieve and dried at 50° C. for approx. 17 hours. After the dried granules had been sieved again, 16.20 g of magnesium stearate were added and the mixture was compressed to tablets with a hardness of 140 to 150 N.

Example 4

110.47 g of microcrystalline cellulose and 81 g of L-HPC were passed through a 0.8 mm sieve and the two substances were then mixed with 586.13 g of gatifloxacin (water content: 7.87 wt. %) in the high-speed mixer for 5 min. The mixture was granulated with 500 ml of an aqueous hydroxypropyl cellulose solution for 1 min at a mixer blade speed of 385 rpm. The moist granules were then passed through a 3 mm sieve and dried at 50° C. for approx. 17 hours. After the dried granules had been sieved again, 16.20 g of magnesium stearate were added and the mixture was compressed to tablets with a hardness of 140 to 150 N.

Example 5

110.47 g of microcrystalline cellulose and 81 g of L-HPC were passed through a 0.8 mm sieve and the two substances were then mixed with 586.13 g of gatifloxacin (water content: 7.87 wt. %) in the high-speed mixer for 5 min. The mixture was granulated with 500 ml of an aqueous hydroxypropyl cellulose solution for 5 min at a mixer blade speed of 385 rpm. The moist granules were then passed through a 3 mm sieve and dried at 50° C. for approx. 17 hours. After the dried granules had been sieved again, 16.20 g of magnesium stearate were added and the mixture was compressed to tablets with a hardness of 140 to 150 N.

Example 6

110.47 g of microcrystalline cellulose and 81 g of L-HPC were passed through a 0.8 mm sieve and the two substances were then mixed with 586.13 g of gatifloxacin (water content: 7.87 wt. %) in the high-speed mixer for 5 min. The mixture was granulated with 500 ml of an aqueous hydroxypropyl cellulose solution for 5 min at a mixer blade speed of 215 rpm. The moist granules were then passed through a 3 mm sieve and dried at 50° C. for approx. 17 hours. After the dried granules had been sieved again, 16.20 g of magnesium stearate were added and the mixture was compressed to tablets with a hardness of 140 to 150 N.

The tablets of Examples 7 to 14 below have a composition according to the invention.

Example 7

102.668 g of microcrystalline cellulose and 40.50 g of L-HPC were passed through a 0.8 mm sieve and mixed with 582.53 g of gatifloxacin (water content: 7.30 wt. %) in a high-speed mixer for 5 min. The mixture was granulated with 300 ml of an aqueous hydroxypropyl cellulose solution (16.20 g) for 1 min at a mixer blade speed of 215 rpm. The moist granules were then passed through a 3 mm sieve and dried at 50° C. for approx. 17 hours. After the dried granules had been sieved again, 11.408 g of microcrystalline cellulose, 40.50 g of L-HPC and 16.20 g of magnesium stearate were added. The granules were compressed to tablets with a hardness of 140 to 150 N.

Example 8

102.668 g of microcrystalline cellulose and 40.50 g of L-HPC were passed through a 0.8 mm sieve and mixed with 582.53 g of gatifloxacin (water content: 7.30 wt. %) in a high-speed mixer for 5 min. The mixture was granulated with 400 ml of an aqueous hydroxypropyl cellulose solution (16.20 g) for 1 min at a mixer blade speed of 215 rpm and the moist granules were passed through a 3 mm sieve and dried at 50° C. for approx. 17 hours. After the dried granules had been sieved again, 11.408 g of microcrystalline cellulose, 40.50 g of L-HPC and 16.20 g of magnesium stearate were added. The granules were compressed to tablets with a hardness of 140 to 150 N.

Example 9

102.668 g of microcrystalline cellulose and 40.50 g of L-HPC were passed through a 0.8 mm sieve and mixed with 582.53 g of gatifloxacin (water content: 7.30 wt. %) in a high-speed mixer for 5 min. The mixture was granulated with 300 ml of an aqueous hydroxypropyl cellulose solution (16.20 g) for 5 min at a mixer blade speed of 215 rpm. The moist granules were then passed through a 3 mm sieve and dried at 50° C. for approx. 17 hours. After the dried granules had been sieved again, 11.408 g of microcrystalline cellulose, 40.50 g of L-HPC and 16.20 g of magnesium stearate were added. The granules were compressed to tablets with a hardness of 140 to 150 N.

Example 10

102.668 g of microcrystalline cellulose and 40.50 g of L-HPC were passed through a 0.8 mm sieve and mixed with 582.53 g of gatifloxacin (water content: 7.30 wt. %) in a high-speed mixer for 5 min. The mixture was granulated with 400 ml of an aqueous hydroxypropyl cellulose solution (16.20 g) for 5 min at a mixer blade speed of 215 rpm. The moist granules were then passed through a 3 mm sieve and dried at 50° C. for approx. 17 hours. After the dried granules had been sieved again, 11.408 g of microcrystalline cellulose, 40.50 g of L-HPC and 16.20 g of magnesium stearate were added. The granules were compressed to tablets with a hardness of 140 to 150 N.

Example 11

102.668 g of microcrystalline cellulose and 40.50 g of L-HPC were passed through a 0.8 mm sieve and mixed with 582.53 g of gatifloxacin (water content: 7.30 wt. %) in a high-speed mixer for 5 min. The mixture was granulated with 300 ml of an aqueous hydroxypropyl cellulose solution (16.20 g) for 1 min at a mixer blade speed of 385 rpm. The moist granules were then passed through a 3 mm sieve and dried at 50° C. for approx. 17 hours. After the dried granules had been sieved again, 11.408 g of microcrystalline cellulose, 40.50 g of L-HPC and 16.20 g of magnesium stearate were added. The granules were compressed to tablets with a hardness of 140 to 150 N.

Example 12

102.668 g of microcrystalline cellulose and 40.50 g of L-HPC were passed through a 0.8 mm sieve and mixed with 582.53 g of gatifloxacin (water content: 7.30 wt. %) in a high-speed mixer for 5 min. The mixture was granulated with 400 ml of an aqueous hydroxypropyl cellulose solution (16.20 g) for 1 min at a mixer blade speed of 385 rpm. The moist granules were then passed through a 3 mm sieve and dried at 50° C. for approx. 17 hours. After the dried granules had been sieved again, 11.408 g of microcrystalline cellulose, 40.50 g of L-HPC and 16.20 g of magnesium stearate were added. The granules were compressed to tablets with a hardness of 140 to 150 N.

Example 13

102.668 g of microcrystalline cellulose and 40.50 g of L-HPC were passed through a 0.8 mm sieve and mixed with 582.53 g of gatifloxacin (water content: 7.30 wt. %) in a high-speed mixer for 5 min. The mixture was granulated with 300 ml of an aqueous hydroxypropyl cellulose solution (16.20 g) for 5 min at a mixer blade speed of 385 rpm. The moist granules were then passed through a 3 mm sieve and dried at 50° C. for approx. 17 hours. After the dried is granules had been sieved again, 11.408 g of microcrystalline cellulose, 40.50 g of L-HPC and 16.20 g of magnesium stearate were added. The granules were compressed to tablets with a hardness of 140 to 150 N.

Example 14

102.668 g of microcrystalline cellulose and 40.50 g of L-HPC were passed through a 0.8 mm sieve and mixed with 582.53 g of gatifloxacin (water content: 7.30 wt. %) in a high-speed mixer for 5 min. The mixture was granulated with 400 ml of an aqueous hydroxypropyl cellulose solution (16.20 g) for 5 min at a mixer blade speed of 385 rpm. The moist granules were then passed through a 3 mm sieve and dried at 50° C. for approx. 17 hours. After the dried granules had been sieved again, 11.408 g of microcrystalline cellulose, 40.50 g of L-HPC and 16.20 g of magnesium stearate were added. The granules were compressed to tablets with a hardness of 140 to 150 N.

What is claimed is:

1. A solid pharmaceutical dosage form for oral administration having a multi-phase structure consisting of an inner phase and at least one outer phase, said inner phase comprising a gatifloxacin compound selected from the group consisting of gatifloxacin, pharmaceutically acceptable salts thereof and hydrates thereof, and at least one auxiliary substance selected from the group consisting of fillers, binders and disintegration aids; and said outer phase comprising at least one disintegration aid and at least one lubricant.

2. A solid pharmaceutical dosage form according to claim 1, wherein said outer phase further comprises at least one filler or at least one binder or both.

3. A solid pharmaceutical dosage form according to claim 1, wherein the gatifloxacin compound comprises from 20 wt. % to 80 wt. % of the solid pharmaceutical dosage form.

4. A solid pharmaceutical dosage form according to claim 3, wherein the gatifloxacin compound comprises from 50 wt. % to 80 wt. % of the solid pharmaceutical dosage form.

5. A solid pharmaceutical dosage form according to claim 1, wherein said at least one outer phase comprises at least 3 wt. % of the solid pharmaceutical dosage form.

6. A solid pharmaceutical dosage form according to claim 1, wherein said inner phase comprises at least one filler selected from the group consisting of lactose, starch, dicalcium phosphate, microcrystalline cellulose, mannitol and dextrose.

7. A solid pharmaceutical dosage form according to claim 1, comprising at least one binder selected from the group consisting of hydroxypropyl methyl cellulose, polyvinylpyrrolidone, hydroxypropyl cellulose and starch mucilage.

8. A solid pharmaceutical dosage form according to claim 1, comprising at least one disintegration aid selected from the group consisting of hydroxypropyl cellulose with a low degree of substitution, crosspovidones, crosscarmelloses, starches, pectins, alginates and surfactants.

9. A solid pharmaceutical dosage form according to claim 1, wherein said at least one outer phase comprises at least one lubricant selected from the group consisting of magnesium stearate, stearic acid, calcium stearate and fatty alcohols.

10. A process for preparing a solid pharmaceutical dosage form for oral administration having multi-phase structure comprising an inner phase and at least one outer phase, said process comprising:

granulating an inner phase mixture comprising a gatifloxacin compound selected from the group consisting of gatifloxacin, pharmaceutically acceptable salts thereof and hydrates thereof, and at least one auxiliary substance selected from the group consisting of fillers, binders and disintegration aids, for from 0.5 to 20 minutes with 20 wt. % to 80 wt. % of a granulating liquid based on the weight of said inner phase mixture, to produce inner phase granules;

drying and sieving the inner phase granules;

mixing the dried and sieved inner phase granules with an outer phase mixture comprising at least one disintegration aid and at least one lubricant, to obtain a resulting mixture, and converting the resulting mixture to a solid pharmaceutical dosage form.

11. A process according to claim 10, wherein said outer phase mixture further comprises at least one filler or at least one binder or both.

12. A process according to claim 10, wherein said inner phase mixture is granulated for from 0.5 to 10 minutes with 20 wt. % to 70 wt. % of granulating liquid based on the weight of the inner phase mixture.

13. A process according to claim 12, wherein said inner phase mixture is granulated for from 1 to 7 minutes with 20 wt. % to 60 wt. % of granulating liquid based on the weight of the inner phase mixture.

\* \* \* \* \*